Sept. 22, 1959 L. L. BROOKS Plant Pat. 1,866

AZALEA PLANT

Filed July 1, 1958

Lenard L. Brooks
Inventor

United States Patent Office

Plant Pat. 1,866

Patented Sept. 22, 1959

1,866

AZALEA PLANT

Lenard L. Brooks, Modesto, Calif.

Application July 1, 1958, Serial No. 746,059

1 Claim. (Cl. 47—60)

This invention is directed to a new and distinct variety of azalea plant, such plant being characterized particularly by its large, wide opening, reflexed-petaled hose-in-hose flowers in a distinctive shade of red, its ease of reproduction on its own roots, its rapid, many branched habit of growth, and its high value as a greenhouse forcing or garden variety.

The instant variety is a cross produced in the experimental section of my nursery at Modesto, California, the cross being made by pollen from an unnamed ledifolia hybrid on an Indica type azalea, the name of which is unknown to me.

The cross as produced was recognized by me as possessing novel characteristics and appeared suitable for commercial use. It was therefore taken for propagation by cuttings, and the plants thus produced carried forward all the distinguishing characteristics of the parent plant. The original reproduction of the variety by cuttings was carried out in the experimental section of my nursery at Modesto, California.

Referring now more specifically to the botanical details of the new and distinct variety of azalea plant, the following is an outline description of the same:

Plant:

*Form.*—Well branched, symmetrical. It developes into a plant of greater breadth than height.

*Growing habit.*—Dense and bushy with an abundance of large, dark green leaves of good texture and weight. It developes quickly into a well shaped, spreading plant with a minimum of pinching.

*Blooming habit.*—Profuse, flowering evenly over the entire plant at the same time when forced in the greenhouse or flowered naturally in the garden. It flowers profusely as a one year old plant.

*Blooming season.*—Plants growing in the outdoor experimental section of my nursery bloom naturally in late March and April. Pinched at the proper time and grown properly it can be forced for Christmas.

Foliage:

*Size.*—Maximum size of mature leaves on thrifty young plants about two and one half inches long and one and three eighths inches wide, each plane having many smaller leaves. As the plants age the average size becomes smaller.

*Color.*—Growing under good conditions, with an ideal pH value, the color of the mature leaves are a deep green, plate 32–H–12, lighter beneath. Young leaves lighter green, plate 21–K–8.

*Shape.*—Ovate, pointed.

*Aspect.*—Glossy and smooth, but has some minute hairs.

*Texture.*—Medium.

*Edge.*—Without serrations, some minute hairs.

*Ribs and veins.*—Normal. The foliage has a general resemblance to that of the ledifolia, but the color is a deeper green and the young leaves do not have the stickiness characteristic of the young leaves of the ledifolia.

Flower:

*Size.*—Three to four inches.

*Borne.*—One to three on each stem.

*Stem.*—Strong.

*Form.*—Hose-in-hose, one flower set within the other. Often the outer hose does not develop fully. Even when fully developed, the outer hose is usually smaller than the inner one, giving the flower almost the appearance of being single. (See Figure 2, left.) The flowers are larger, open wider, are less vase formed and the petals are more reflexed than most other azalea varieties with flowers of hose-in-hose form.

*Permanence.*—Long lasting, retaining its beauty until the flowers are ready to fall.

*Petalage.*—Five petals on each hose or flower.

Figure 1:
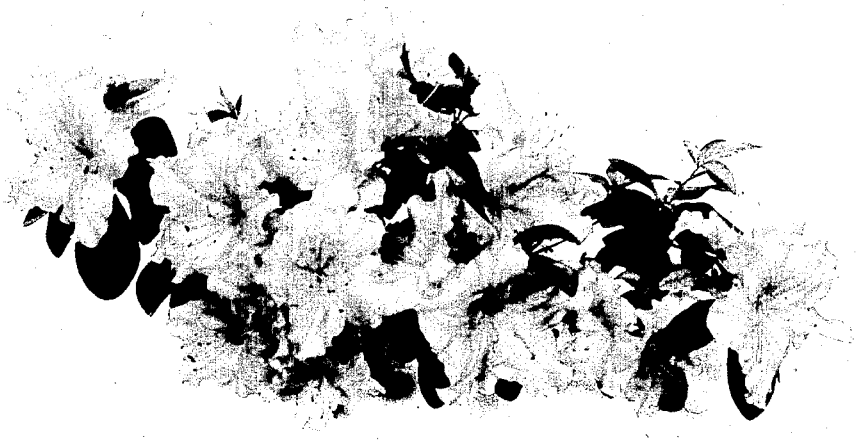
Figure 1 is a perspective view showing a plant in full flower, about one-third natural size.
Figure 2:
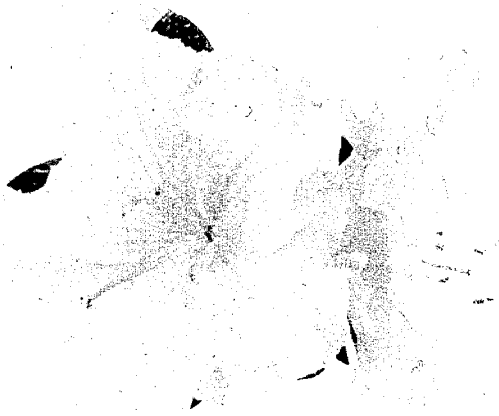
Figure 2 is a perspective view showing a stem with flowers in about their natural size.

*Color.*—Red, plate 4–B–6, veins in a deeper shade, as shown in Fig. 2. There is an undertone of orange, which gives the colors a lively appearance. Fig. 1 shows the flowers in very nearly their natural color when flowered under normal conditions.

Petals:

*Texture.*—Substantial.

*Appearance.*—Velvety, inside and out.

*Size.*—Two to two and one half inches long. One and one-quarter to one and one-half inches wide.

*Shape.*—Broadly ovate.

*Arrangement.*—Normal for its type.

*Persistence.*—Remains firm until the flower is ready to fall.

Reproductive organs:

*Stamens.*—Five is the normal number of stamens for a hose-in-hose azalea flower, but this variety will sometimes have as many as eight and these at times develop embryo petaloids at the base and very rarely these develop into small petaloids. Filament is about the same color as the petals. Anther is maroon. Pollen is white and freely produced. The flower at right in Fig. 2 had developed six stamens.

*Pistil.*—One and one-half to one and three-quarter inches long. Style is about the same color as the petals.

*Ovule.*—Well developed.

All color plate identifications refer to "a Dictionary of Color" by Maerz and Paul.

Compared to other well known azalea varieties, this plant has some characteristics similar to my variety Redwing, Plant Patent No. 1,159, but is distinguished by the following principal differences:

(1) The color of the flowers is deeper, having much more blue and less of the orange shades.

(2) The flower opens wide and flat as in the Belgian Indica type azalea, rather than the trumpet share of the Kurume type as found in Redwing, Patent No. 1,159.

(3) The petals are ruffled, but to a much less degree than found in Redwing, Plant Patent No. 1,159.

(4) The foliage has a strong resemblance to that of the ledifolia azalea, rather than the Kurume azalea aspect as found in Redwing, Plant Patent No. 1,159.

(5) This variety has a much more compact habit of growth than that found in Redwing, Patent No. 1,159.

(6) This variety was produced by using pollen from a ledifolia azalea (name, if any, not known to me) with nearly single flowers in an orchid shade, on a Belgian Indica (name not known to me), with double flowers in a deep shade of pink, while Redwing, Plant Patent No. 1,159, was produced by using pollen from the Kurume azalea Hexe (not patented) on the nearly single, deep orange flowered Belgian Indica azalea Wm. Van Orange (not patented).

Having thus described the invention, I claim:

A new and distinct variety of azalea plane substantially as herein shown and described, characterized particularly by its large, wide opening, hose-in-hose flowers in a distinctive shade of red with an orange undertone, its ample dark green foliage, the ease with which it grows on its own roots, its rapid yet much branched habit of growth, and its high value as a greenhouse forcing and garden variety.

References Cited in the file of this patent

UNITED STATES PATENTS

P.P. 1,159 Brooks ---------- Dec. 23, 1952